United States Patent
Petegnief et al.

(10) Patent No.: US 12,171,565 B2
(45) Date of Patent: Dec. 24, 2024

(54) HYBRID INTRACEREBRAL ELECTRODE

(71) Applicant: DIXI MEDICAL, Chaudefontaine (FR)

(72) Inventors: Lucie Petegnief, Besancon (FR); Jérémy Fumey, Besancon (FR)

(73) Assignee: DIXI MEDICAL, Chaudefontaine (FR)

( * ) Notice: Subject to any disclaimer, the term of this patent is extended or adjusted under 35 U.S.C. 154(b) by 825 days.

(21) Appl. No.: 17/417,323

(22) PCT Filed: Feb. 12, 2020

(86) PCT No.: PCT/EP2020/053556
§ 371 (c)(1),
(2) Date: Jun. 22, 2021

(87) PCT Pub. No.: WO2020/165223
PCT Pub. Date: Aug. 20, 2020

(65) Prior Publication Data
US 2022/0047203 A1 Feb. 17, 2022

(30) Foreign Application Priority Data
Feb. 15, 2019 (FR) ..................... 1901571

(51) Int. Cl.
*A61B 5/37* (2021.01)
*A61B 5/293* (2021.01)
*A61B 5/384* (2021.01)

(52) U.S. Cl.
CPC ............... *A61B 5/37* (2021.01); *A61B 5/293* (2021.01); *A61B 5/384* (2021.01)

(58) Field of Classification Search
CPC .. A61B 5/293; A61B 5/31; A61B 5/37; A61B 5/384; A61B 5/6868; A61B 5/4064;
(Continued)

(56) References Cited

U.S. PATENT DOCUMENTS

| 5,293,869 A | 3/1994 | Edwards et al. |
| 6,332,880 B1 | 12/2001 | Yang et al. |

(Continued)

FOREIGN PATENT DOCUMENTS

| EP | 1062973 A1 | 12/2000 |
| EP | 0971768 B1 | 7/2004 |

(Continued)

OTHER PUBLICATIONS

International Search Report issued in PCT Patent Application No. PCT/EP2020/053556 dated Apr. 6, 2020.

*Primary Examiner* — Eric F Winakur
*Assistant Examiner* — Abel Seifu Abegaz
(74) *Attorney, Agent, or Firm* — MARSHALL, GERSTEIN & BORUN LLP

(57) ABSTRACT

The invention relates to a hybrid intracerebral electrode comprising a narrow, elongated body intended to be implanted in the brain of a patient in order to carry out at least one multi-scale electroencephalographic exploration. Said hybrid intracerebral electrode comprises, in its active part, a plurality of first electrical contact elements forming stationary macro-contacts, and a plurality of second electrical contact elements forming movable micro-contacts. The hybrid intracerebral electrode is characterised by control means which are built into the electrode in a coupling tip integral with the body. The control means are designed to move the second electrical contact elements between a passive position in which same are retracted inside the body and an active position in which same protrude outside the body, and simultaneously to adjust the controlled projection length thereof with respect to the body of the electrode.

17 Claims, 7 Drawing Sheets

(58) Field of Classification Search
CPC ... A61B 5/4082; A61B 5/4088; A61B 5/4094; A61B 5/6846; A61B 5/6848; A61B 5/6849; A61B 5/6859; A61B 2017/00367; A61B 2017/00389; A61B 2017/00455; A61B 2018/0091
See application file for complete search history.

(56) References Cited

U.S. PATENT DOCUMENTS

| | | |
|---|---|---|
| 8,435,079 B1 | 5/2013 | Osa et al. |
| 2006/0229686 A1* | 10/2006 | Giftakis ............... A61B 5/6864 607/45 |
| 2008/0027346 A1* | 1/2008 | Litt .................... A61N 1/36064 600/544 |
| 2010/0191305 A1 | 7/2010 | Imran et al. |
| 2017/0080210 A1 | 3/2017 | Mercanzini et al. |
| 2019/0232050 A1* | 8/2019 | Boers ....................... A61B 5/24 |

FOREIGN PATENT DOCUMENTS

| | | |
|---|---|---|
| JP | 2007111118 A | 5/2007 |
| WO | WO-2003/028521 A2 | 4/2003 |
| WO | WO-2004/096314 A2 | 11/2004 |
| WO | WO-2013/148637 A1 | 10/2013 |

\* cited by examiner

HYBRID INTRACEREBRAL ELECTRODE

TECHNICAL FIELD

This invention relates to a hybrid intracerebral electrode comprising a narrow, elongated body along a longitudinal axis, intended to be implanted in the brain of a patient in order to perform at least one multi-scale electroencephalographic exploration, and a mounting means designed to fix said body to the skull of the patient, said electrode having a distal end and a proximal end, and an active part on the distal end side, said active part being provided with at least one first electrical contact element forming a fixed macro-contact, arranged on the surface of said body and used at least to record the overall activity of an area of the brain under study, and of at least one second electrical contact element forming a mobile micro-contacts, protruding outside said body over a controlled projection length, and used at least to record the activity of small cell groups or even of a single neuron in said area of the brain under study, said at least one first electrical contact element and said at least one second electrical contact element each being electrically connected to at least one recording device by a dedicated conductor wire, said electrode further comprising means for controlling the relative position of said at least one second electrical contact element relative to the body of the electrode.

BACKGROUND

The intracerebral electrodes, called deep electrodes, are intended to be connected as a priority to a recording and/or stimulation device. They are widely used to perform investigations via, for example, stereoelectroencephalography (SEEG) and brain stimulations in order to record brain activity, and detect and delimit areas to be treated in the brain, in particular, areas of dysfunction causing neurological or psychiatric symptoms. These intracerebral electrodes may also be provided for treating said areas of the brain which have been detected, via a treatment using stimulation, thermolesion, or any other treatment method that is adapted to the identified pathology. For this purpose, these deep electrodes are generally equipped with one or preferably a plurality of first electrical contact elements, in the form of, for example, electrical contact pads, distributed axially along the active zone of the body of the electrode. These contact pads form "macro-contacts" which make it possible to record cerebral activity of an area of the brain in order to stimulate and/or treat said area. Certain deep electrodes have advantageously been completed by one or a plurality of second electrical contact elements, for example in the form of the end of one or a plurality of conductor wires forming "micro-contacts" which make it possible to record the cerebral activity of small cell groups, or even of a single neuron, to stimulate and/or treat these small cell groups or this single neuron, in the area of the brain being explored. These intracerebral electrodes combining the two types of electrical contact elements are commonly called "hybrid" electrodes and have the advantage of making clinical neurophysiological explorations of the brain at different precision scales possible by using the same medical device, and/or clinical treatment at different precision scales. For example, in the context of epileptic pathologies, this so-called "multi-scale" exploration may make it possible to more precisely identify the epileptogenic and/or functional zones in order to establish a more accurate diagnosis of the area to be treated surgically. In fact, it has been found that during stereoelectroencephalography (SEEG), high frequency oscillations beyond 80 Hz ("ripples"), or very high frequency oscillations beyond 200 Hz ("fast ripples") may be recorded, and that very high frequency "ripples" seem to be new biomarkers of epileptogenic areas. These "ripples" are usually recorded by the first electrical contact elements (macro-contacts or macro-electrodes with, for example, a diameter or transverse dimension of approx. 800 µm), however, the second electrical contact elements (micro-contacts or micro-electrodes with, for example, a diameter or transverse dimension of approx. 20 µm) make their detection easier. Thus, the use of such a hybrid electrode may, for instance, result in resection surgery of the pathogenic foci by thermolesion or any other suitable treatment method, determine favourable areas for the implantation of deep stimulation electrodes called "DBS" ("Deep Brain Stimulation"), or perform any other intervention on the pathogenic foci depending on the diagnosed pathology.

The following publications, among others, provide a better understanding of how valuable this technology is in the treatment of epilepsy: Interictal High-Frequency Oscillations (80-500 Hz) in the Human Epileptic Brain: Entorrhinal Cortex (Anatol Bragin et al., An Neurol 2002; 52: 407-415); High-frequency oscillations in human temporal lobe: simultaneous microwire and clinical macroelectrode recordings (Greg A. Worrell et al., Brain (2008), |3|, 928-937).

Publications U.S. Pat. No. 8,435,079 B1 and WO 2004/096314 A2 describe hybrid electrodes in which the micro-contacts are flush with the peripheral surface of the body of the electrode between the consecutive contact pads, without being projecting or being retractable. Publications EP 0971768 A1 and EP 1062973 A1 describe hybrid electrodes equipped with a single axial micro-contact, projecting at the distal end of the body of the electrode, integral with a movable and removable stylus. Publication WO 2003/028521 A2 proposes a hybrid electrode provided with a plurality of micro-contacts projecting axially and radially from the body of the electrode between consecutive contact pads, without adjustment means or projection length control.

In another application, publication WO 2013/148637 A1 proposes a cortical detection grid, designed to be in contact with the surface of the brain, and in which each micro-contact is positioned inside a macro-contact, in a coplanar and coaxial manner.

The hybrid intracerebral electrodes which currently exist are not entirely satisfactory. They may damage brain tissue when being inserted, require modifications to the implantation protocol, or lose clinical information.

SUMMARY OF THE DISCLOSURE

The present invention aims to overcome these disadvantages by proposing a hybrid intracerebral electrode solution designed to perform multi-scale and multi-point neurophysiological explorations making it possible to identify and/or diagnose and/or stimulate and/or treat defective areas of the brain with very high level of precision, by a means for adjusting the relative position of the micro-contacts that is simple, ergonomic, precise, integrated into the electrode and easily accessible to the practitioner, so that he may act in real time on the output or not of the micro-switches, and on the projection length throughout the implantation period of the electrode. Furthermore, this new hybrid electrode solution is completely compatible with conventional implantable electrodes, and consequently has no impact on the implantation protocols being used to date.

For this purpose, the invention relates to a hybrid intracerebral electrode of the type indicated in the preamble, characterised in that it comprises, at its proximal end, a coupling tip integral with said body and on which is mounted said means for controlling the relative position of said at least one second electrical contact element so that they form an integral part of said electrode, and in that said control means is arranged firstly to move said at least one second electrical contact element between a passive position in which it is retracted inside said body and an active position in which it projects outside said body, and secondly to adjust the controlled projection length of said at least one second electrical contact element relative to said body of the electrode.

Thanks to this embodiment, the projection length of the micro-contacts is not fixed before implantation. It may be adjusted and controlled after implantation. This feature makes it possible to have micro-contacts flush with the body of the electrode (passive position) during the insertion of the electrode so as not to damage the brain tissues, then, once the electrode is in position in the brain, in order to be able to progressively move the micro-contacts and vary their projection length depending on the results of the investigations (active position) throughout the duration of implantation, and finally, when the electrode is explanted, to retract these micro-contacts flush with the body of the electrode (passive position) so as not to damage any brain tissues.

In a preferred embodiment of the invention, said control means comprise at least one driving member movable in rotation relative to said coupling tip around a rotation axis coincident with the longitudinal axis of said body, and a driven member coupled to said driving member so as to be displaced in reciprocating axial translation in the direction of rotation of said driving member, and said driven member is integral with said at least one second electrical contact element so that it is movable in translation along the longitudinal axis of said body over a stroke at least equal to its controlled projection length.

In a first embodiment, said driving member may take the form of a thumbwheel, which can be actuated manually, coupled in rotation with said coupling tip by a thread, and movable in translation relative to said coupling tip. In this case, said driven member may take the form of a pusher actuated in one direction and in an opposite direction depending on the direction of rotation of said driving member.

In a second embodiment, said driving member may take the form of a thumbwheel which may be actuated manually, coupled in rotation with said coupling tip by a guide surface, and fixed in axial translation relative to said coupling tip. In this case, said driven member may take the form of an adjusting screw guided axially in said coupling tip, coupled in translation with said driving member by a thread, and fixed in rotation relative to said driving member.

In a variant embodiment of the invention, said control means may comprise at least one driving member movable in reciprocating axial translation relative to said coupling tip along an axis parallel to or coincident with the longitudinal axis of said body, and a driven member coupled to said driving member so as to be displaced in reciprocating axial translation in the direction of displacement of said driving member, said driven member being integral with said at least one second electrical contact element so that it is movable in translation along the longitudinal axis of said body over a stroke at least equal to its controlled projection length.

Advantageously, said control means may comprise stroke limiters arranged to control the axial displacement of said driven member over a stroke that is at least equal to the controlled projection length of said at least one second electrical contact element. They may comprise at least one axial slot extending over a length corresponding to said stroke and cooperating with at least one guide pin, said axial slot being provided in one of the parts of said driven member or of said coupling tip, and said guide pin being provided in the other part of said coupling tip or of said driven member.

Said coupling tip preferably comprises a central bore in which said driven member is guided in axial translation and said central axial bore defines a reserve in which the conductor wire dedicated to said at least one first electrical contact element may accumulate in order to absorb the travel of said driven member.

Said control means may advantageously comprise means for locating the outlet position of said at least one second electrical contact element. They may comprise an integral slider of said at least one second electrical contact element and arranged to slide axially in a guide bore of said coupling tip or of said driving member, said slider comprising a marking and said guide bore comprising at least one through-hole for displaying said marking.

In the preferred embodiment of the invention, said body comprises at least one outlet port provided in the active part of the electrode, through which said at least one second electrical contact element projects outside said body in the active position.

The active part of the electrode may advantageously comprise a plurality of first electrical contact elements distributed along the body of the electrode and separated from each other by insulating intermediate elements, and said at least one second electrical contact element projects through said at least one outlet port provided in one of said insulating intermediate elements and/or in one of said first electrical contact elements.

Said at least one outlet port is advantageously provided on the periphery of said body and said at least one second electrical contact element projects radially outside said body relative to said longitudinal axis.

Unlike the only axially projecting micro-contacts of the hybrid electrodes of the prior art, the micro-contacts projecting radially relative to the longitudinal axis have the advantage that they can be positioned all along the active part of the electrode in order to adapt to all implantations (deep or shallow areas of interest) without having to modify the protocol for implanting the macro-contacts and they make better spatial correspondence possible between microscopic and macroscopic analyses.

According to the variant embodiments, the active part of the electrode may comprise at least two second electrical contact elements distributed radially around said body.

In addition, said active part may comprise a plurality of second electrical contact elements grouped at least in pairs so as to leave via the same outlet port, and for example groups of four second electrical contact elements arranged side by side so as to form a tetrode.

The active part may also comprise a plurality of outlet ports distributed over at least two levels along the body of the electrode. In which case, said control means may be arranged to individually or simultaneously control the second electrical contact elements by level.

BRIEF DESCRIPTION OF THE FIGURES

The present invention and the advantages thereof will appear more clearly in the following description of a plurality of embodiments given for purposes of illustration only and not intended to limit the scope of the invention, with reference to the accompanying drawings, wherein.

DETAILED DESCRIPTION

In the embodiments shown, identical elements or parts bear the same reference numbers. Furthermore, the variants described for the different embodiments of the invention may be combined with one another.

Figure 7:
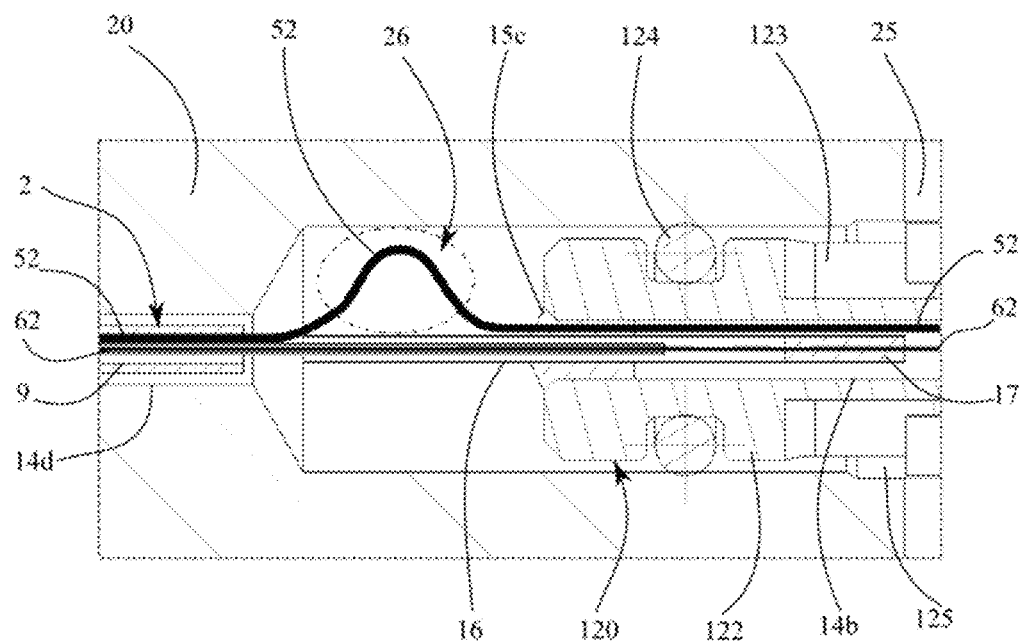
FIG. 7 is an enlarged view of detail VII in FIG. 6.
Figure 8:
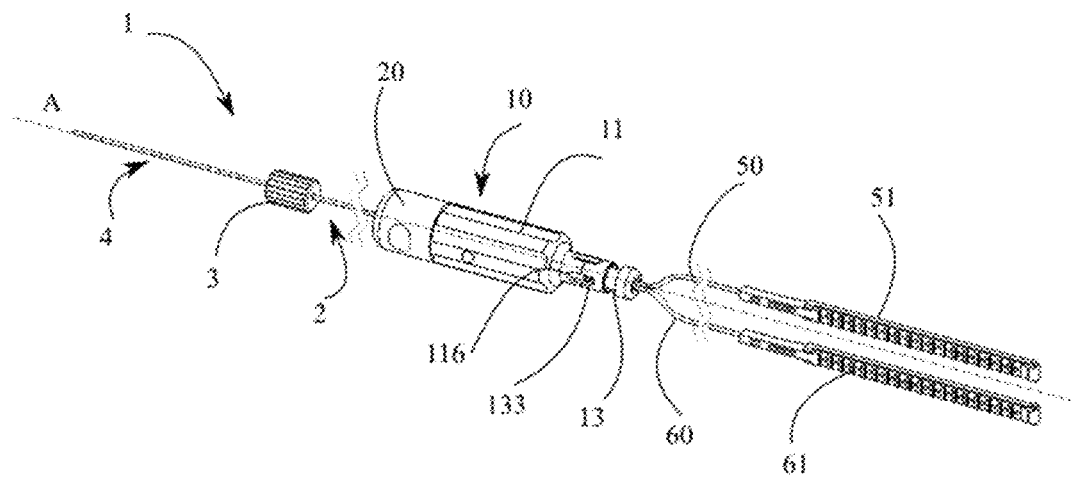
FIG. 8 is a perspective view of the electrode in FIG. 1, partially cut, and seen from the side of the electrical connectors.
Figure 9:
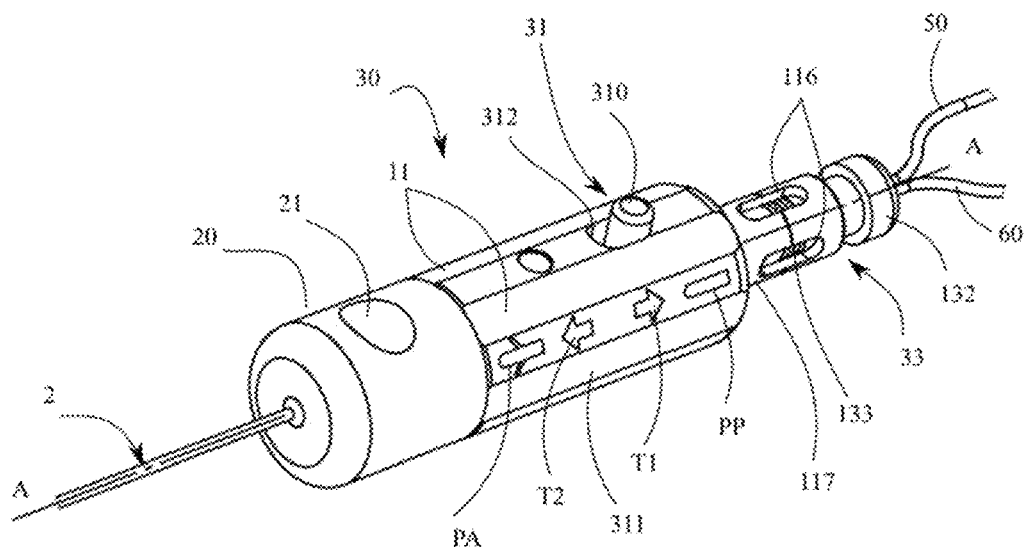
FIG. 9 is a perspective view of the control means of the micro-contacts according to a variant embodiment, in a position corresponding to the passive position of the micro-contacts.
Figure 10:
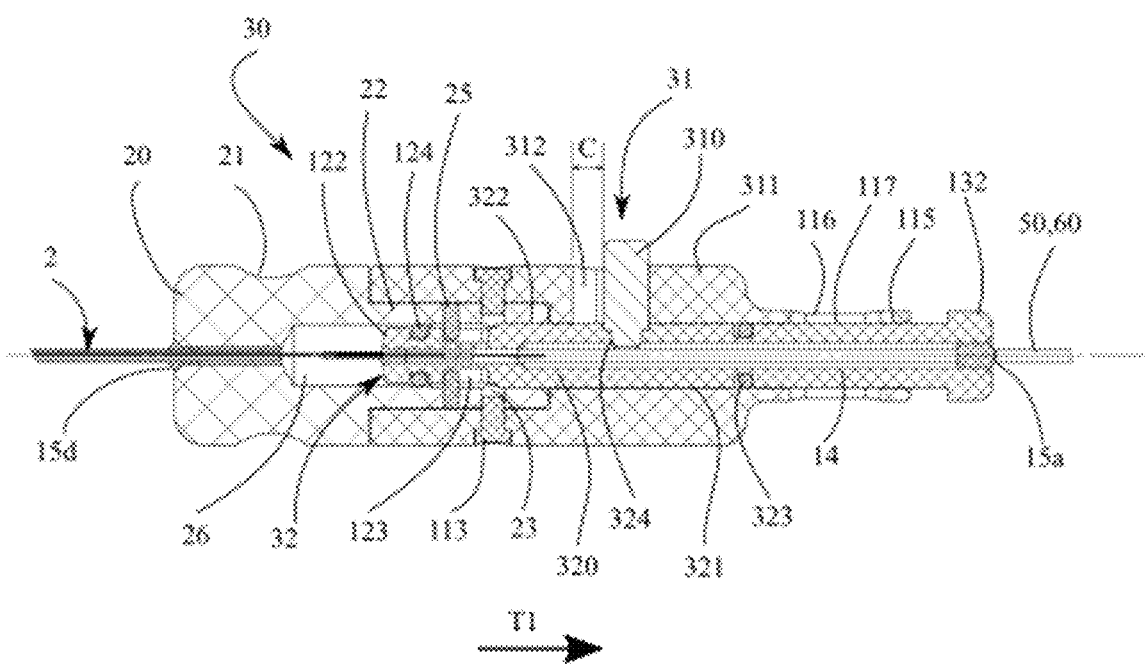
FIG. 10 is an axial cross-sectional view of the control means in FIG. 9.
Figure 11:
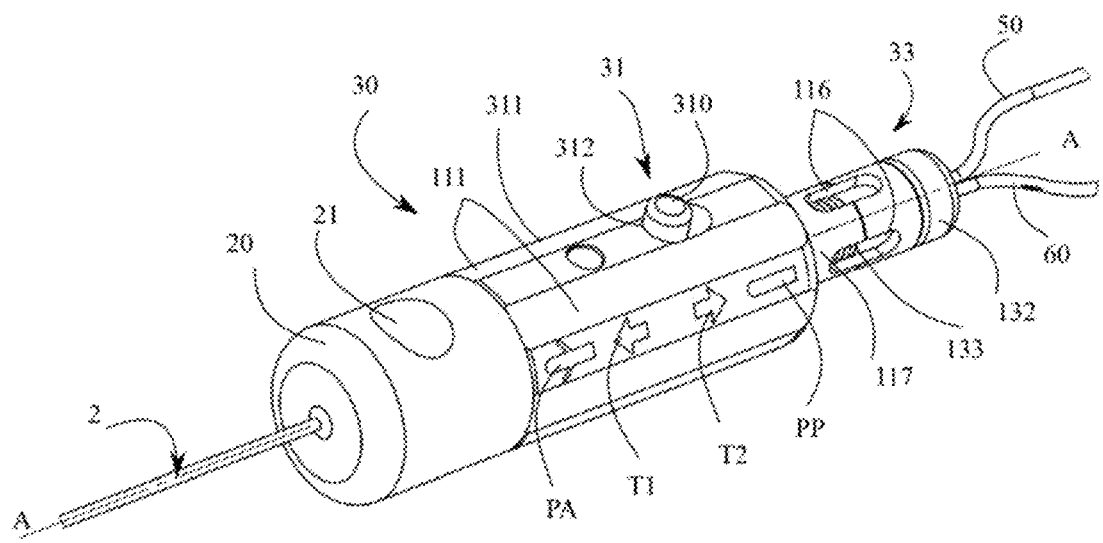
FIG. 11 is a perspective view of the control means of the micro-contacts in FIG. 9, in a position corresponding to the active position of the micro-contacts.
Figure 12:
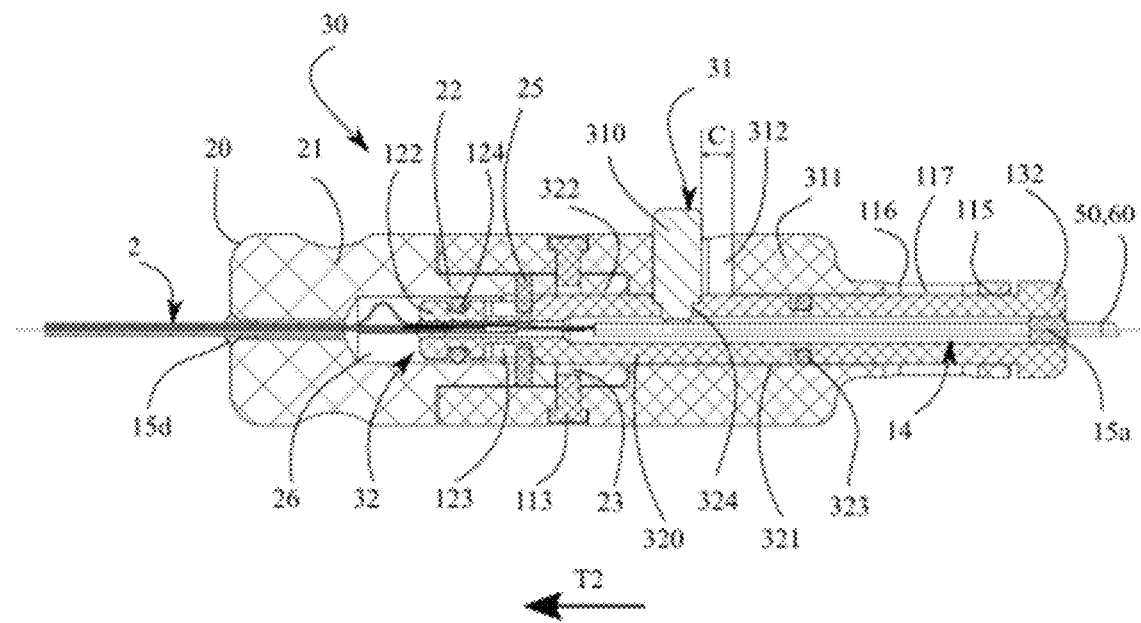
FIG. 12 is an axial cross-sectional view of the control means in FIG. 11.

With reference to FIGS. 1 to 4, the hybrid intracerebral electrode 1 according to the invention, referred from now on as the "electrode 1", comprises a narrow and elongated needle-shaped body 2 intended to be implanted at least partially in the brain of a patient in order to perform at least one multi-scale electroencephalographic exploration. It comprises a plug 3 which performs a plurality of functions: adjusting the depth of insertion of the electrode 1, maintaining the electrode 1 in position implanted on a screw or similar previously anchored to the skull of the patient, and ensuring the sealing of the electrode 1 by preventing any leakage of cerebrospinal fluid. The body 2 of the electrode 1 comprises an active part 4, corresponding to its distal end zone which is implanted into the brain. The active part 4 comprises at least one and preferably a plurality of first fixed electrical contact elements 5, in the form of contact pads or macro-contacts, arranged on the surface of the body 2, and used at least to record the activity of an area of the brain under study. It further comprises at least one and preferably a plurality of mobile second electrical contact elements 6, in the form of micro-contacts or micro-electrodes, projecting outside the body 2 and used at least to record the activity of small cell groups or even of a single neuron in the area of the brain under study. According to the number of second electrical contact elements (6), a point measurement or a multi-point measurement is obtained. Each group of electrical contact elements 5 and 6 is connected to a medical device which may be a recording device, such as an electroencephalograph or any other device for measuring brain activity, a treatment device, such as a high-frequency generator, or similar, for performing, for example, a thermolesion by thermo-coagulation, a stimulation device, or any other treatment of the brain area to be treated. These various medical devices and the electrical contact elements 5 and 6 are interconnected by conductor wires 52, 62, which pass through said body 2 in an axial housing 9 (FIG. 7) coincident with the longitudinal axis A and extending from the distal end to the proximal end of the electrode 1. Outside the electrode 1, the conductor wires 52, 62 are assembled in multi-wire sheaths 50, 60 and connected to dedicated multi-contacts 51, 61, compatible with the connected medical device.

The first electrical contact elements 5 form "macro-contacts" or "macro-electrodes" as opposed to the second electrical contact elements 6 which form "micro-contacts" or "micro-electrodes" whose contact surface is infinitely small compared to that of the "macro-contacts". For example only, the first electrical contact elements 5 may have a diameter of 800 µm and a length of 2 mm, whereas the second electrical contact elements 6 may have a transverse dimension of 20 µm. Thus, the surface area ratio between the "macro-contacts" and the "micro-contacts" may be very high and, for example, be approx. $16000^e$, without the values stated being limiting.

Each first electrical contact element 5 is made of electrically conductive materials, preferably permeable to magnetic radiation, such as, by way of non-limiting examples, titanium, titanium-nickel alloys, graphite carbon, cobalt-based alloys, tantalum, platinum, platinum-iridium alloys, non-ferrous alloys based on copper, nickel-zinc alloys, zamak and copper-beryllium alloys, or similar. The first electrical contact elements 5 may be formed by pads, patches, rings, or any other part equivalent in shape, each connected to one of the conductor wires 52. They may be assembled together and/or to said body 2 of the electrode 1 by layering, gluing, crimping, overmoulding, or any other suitable assembly method. In the embodiment shown, the first contact elements 5 are formed by conductive rings interposed with insulating rings in order to form the active part 4 of the electrode 1. The insulating rings advantageously form insulating intermediate elements 7, which may be made differently depending on the embodiment of said first contact elements 5. In variant embodiments (not shown), the first electrical contact elements 5 may be made by any other suitable manufacturing process, such as, for example, by physical deposition of metal under vacuum (PVD), by semiconductor technology (MEMS: Microelectromechanical systems), or any other equivalent process. In this case, the insulating intermediate elements 7 may be constituted directly by the body 2 of the electrode 1. The first electrical contact elements 5 are distributed along the body 2 of the electrode 1, and preferably in its active part 4. They may or may not be identical, and may or may not be spaced apart by a regular pitch, this pitch being determined particularly by the insulating intermediate elements 7. They may or may not also comprise a first electrical contact element 5 at the distal end of said body 2. The techniques for manufacturing these first contact elements 5 may correspond to those already used in known deep electrodes, or they may make use of new technologies.

Figure 1:
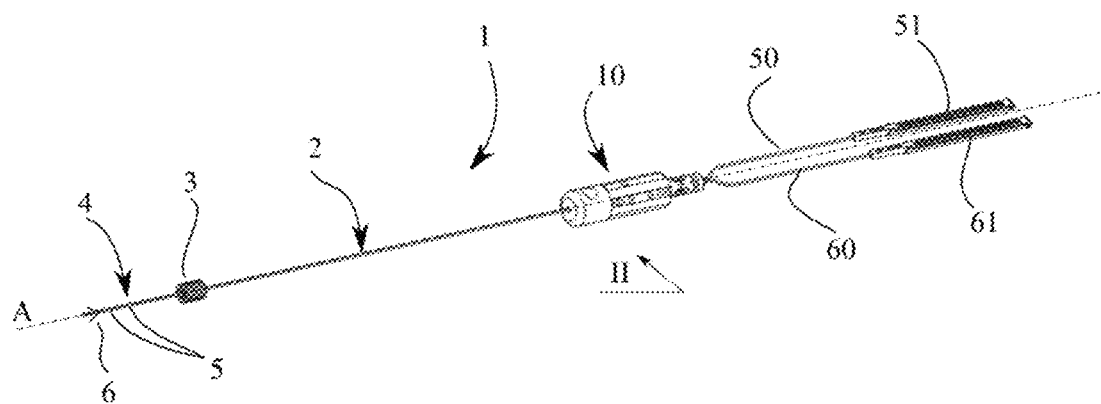
FIG. 1 is a perspective view of a hybrid intracerebral electrode according to the invention.
Figure 2:
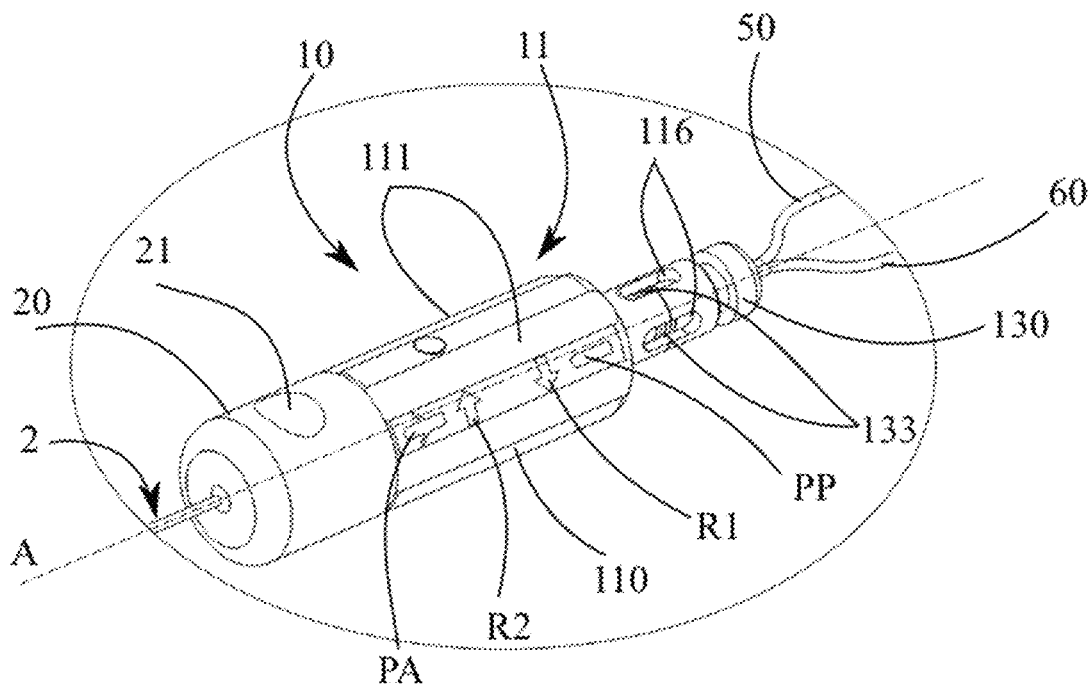
FIG. 2 is an enlarged view of the control means of the micro-contacts according to detail II in FIG. 1.
Figure 3:
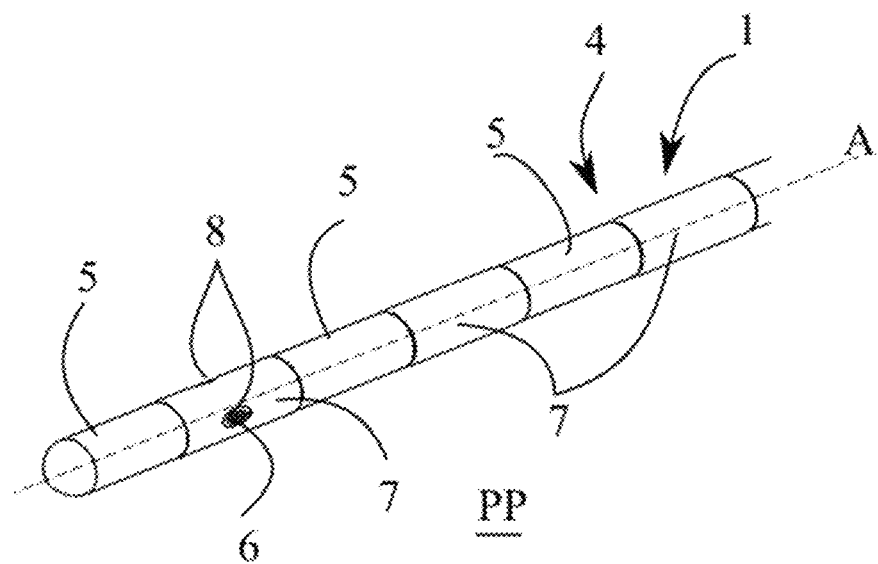
FIG. 3 is an enlarged view of the distal end of the electrode in FIG. 1, showing the micro-contacts in the passive position, retracted inside the electrode.
Figure 4:
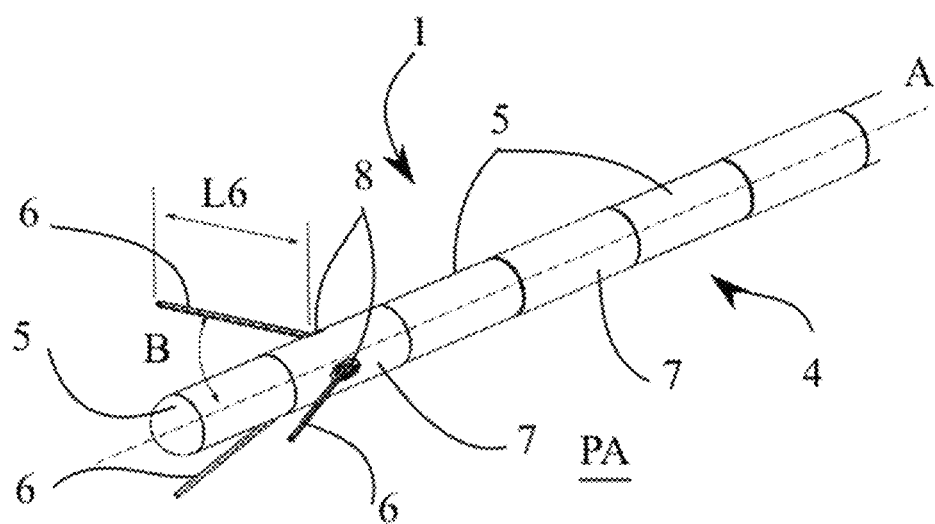
FIG. 4 is a similar view to FIG. 3, showing the micro-contacts in the active position, projecting outside the electrode.

Each second electrical contact element 6 is constituted by the end of at least one very fine conductor wire 62 made of electrically conductive materials, measuring approx. 20 µm, but not limited to this size. These materials are preferably also permeable to magnetic radiation, such as those listed above in terms of the first electrical contact elements 5, in order to be compatible with medical magnetic resonance imaging devices. Each second electrical contact element 6 is preferably constituted by the end of a conductor wire 62. Of course, it is possible to multiply the number of conductor wires 62, each then forming a second electrical contact element 6 by itself and each being connected to a terminal of the multi-contact connector 61. In the example shown, the second electrical contact elements 6 are arranged in groups of four, positioned side by side, and form a tetrode. This example is non-limiting and it is possible to group two, three or more than four conductor wires 62 to adapt the number and distribution of the second electrical contact elements 6 to the technical specifications of the electrode 1. The second electrical contact elements 6 arranged in the axial housing 9 of said body 2 are provided to project outside said body 2 at least radially relative to the longitudinal axis A. The term "radially" must be understood in contrast to the term "axially" but without necessarily implying an angle of 90° between the projecting part of the second electrical contact elements 6 and the longitudinal axis A of the body 2. For example, FIG. 4 illustrates the active position of the second electrical contact elements 6 in which their projecting part is orientated towards the distal part of said body 2 and forms an angle B with the longitudinal axis A different from 90°, and particularly an acute angle, but this example is non-limiting. Any other arrangement of the second electrical contact elements 6 relative to said body 2 and/or relative to said first electrical contact elements 5 may be envisaged. For example, the second electrical contact elements 6 may move from the first electrical contact elements 5. In addition, it is possible to add one or a plurality of second electrical contact elements 6 projecting axially outside the distal end of said body 2 in the longitudinal axis A of the body 2. For this purpose, the body 2 comprises outlet ports 8 arranged in said active part 4, radially and/or axially, in one or a plurality of insulating intermediate elements 7 and/or in one or a plurality of first electrical contact elements 5, to make it possible for there to be an outlet for the second electrical contact elements 6 over a controlled length L6 (see FIG. 4). These outlet ports 8 may or may not be distributed around the body 2 at regular intervals, from the distal end at the same distance or otherwise. In the example shown, the electrode 1 comprises three second electrical contact elements 6, distributed at 120° around the body 2, in the insulating intermediate element 7 closest to the distal end of the electrode 1, between the first electrical contact element 5 provided at the distal end of the electrode 1 and the following first electrical contact element 5. Of course, this example is non-limiting and any other arrangement along the active part 4 of the electrode 1 may be appropriate.

The body 2 of the electrode 1 is constituted by a hollow tube which delimits said axial housing 9 and forms a protective sheath for the conductor wires 52, 62 of the first and second electrical contact elements 5, 6. In addition, each of the conductor wires 52 and/or 62 may be individually insulated. Preferably, it is made of a synthetic material providing it with both good mechanical strength and a certain flexibility, and is electrically insulating. Examples of preferable synthetic materials are polyamides, polyether block amides, polycarbonates, polyimides, polytetrafluoroethylenes, or similar. It may have a circular section, or any other section that is compatible with the intended applications. Its transverse dimension is preferably very small, in particular measuring less than one millimetre, for example approx. 800 µm.

The electrode 1 according to the invention further comprises control means 10 for moving the second electrical contact element or elements 6 simultaneously between a passive position PP in which they are retracted inside the body 2 (see FIG. 3), and an active position PA in which they project outside the body 2 over a controlled projection length L6 (see FIG. 4) and make it possible in particular to record electroencephalographic activity of small cell groups or even of a single neuron. This controlled projection length L6 is thus made adjustable, for example by 0 and 5 mm, without these values being limiting, and this throughout the implantation period of the electrode 1, i.e. until the explanation of the electrode 1. These control means 10 are accessible to the practitioner to make it possible for him to intervene in real time in the position of the second electrical contact elements 6 during exploration and/or stimulation and/or treatment. They form an integral part of the electrode 1, in that they are connected to the body 2 of the electrode 1 and are neither dissociated nor removable from the body 2.

In the example shown in FIGS. 1 to 8, the control means 10 comprise a driving member 11 movable in rotation relative to the body 2 around a rotation axis coincident with the longitudinal axis A of said body 2. They also comprise a driven member 12 coupled to the driving member 11 so as to be displaced in reciprocating axial translation in the direction of the arrows T1, T2 depending on the direction of rotation R1, R2 of the driving member 11 (see FIGS. 2, 5 and 6). The driven member 12 is integral with the second electrical contact elements 6 so that they may move simultaneously in translation along the longitudinal axis A of said body 2 over a stroke C at least equal to their controlled projection length L6.

In this example, the driving member 11 takes the form of a thumbwheel 110, preferably cylindrical, that has a sufficient diameter so that it can be manually actuated by the practitioner. For this purpose, the gripping surface of this thumbwheel 110 has reliefs 111 so that it may be grasped easier without any sliding. The driving member 11 is coupled in rotation with the body 2 of the electrode 1 that is fixed. For this purpose, a coupling tip 20 is fixed to the end of said body 2 corresponding to the proximal end of the electrode 1, in order to carry said thumbwheel 110. This coupling tip 20 is preferably cylindrical and has a diameter substantially equal to the diameter of the thumbwheel 110, a diameter substantially greater than that of said body 2 so that it may be grasped easier. This coupling tip 20 comprises a fingerprint 21, and preferably two diametrically opposite fingerprints 21, making it possible for it to be grasped without sliding in order for it to be held in a fixed position with one hand while the other hand rotates the driving member 11, in one direction or in the opposite direction, according to the arrows R1 and R2 symbolised on the thumbwheel 110. For example, rotating the driving member 11 firstly in the direction of the arrow R1 moves the driven member 12 back and retracts the second electrical contact elements 6 to the passive position PP, in accordance with the symbol represented on the thumbwheel 110. In addition, the rotation of the driving member 11 in the opposite direction according to the arrow R2 leads to advancing the driven member 12 and moving the second electrical contact elements 6 to the active position PA, in accordance with the symbol represented on the thumbwheel 110. Of course, the shape of the thumbwheel 110 and that of the coupling tip 20 may not have a cylindrical shape, and it is essential that this shape be ergonomic and easy to maintain and handle.

In the example shown in FIGS. 1 to 8, the coupling tip 20 integral with said body 2 comprises a smooth cylindrical guide section 22 extending in the opposite direction to the distal end of the electrode 1, and on which the driving member 11 is mounted in rotation via a cylindrical bore 112, so that it is guided in rotation around the longitudinal axis A. The driving member 11 is fixed in translation relative to said body 2 by means of two diametrically opposite shouldered pins 113 housed in corresponding holes provided in the thumbwheel 110 and in a plane perpendicular to the longitudinal axis A. The end of the shouldered pins 113 cooperates with an annular groove 23 provided on the outer face of the guide section 22 of the coupling tip 20. Of course, any other means for locking the driving member in translation 11 relative to said body 2 may be suitable.

Always in this example, the driven member 12 takes the form of an adjusting screw 120 precise to the nearest millimetre, making it possible to very precisely adjust the position of the second electrical contact elements 6 within the nervous tissue. The driven member 12 is, on the one hand, coupled to the driving member 11 by a threaded section 121 screwed into a tapped bore 114 of the driving member 11, coaxial with the longitudinal axis A. The driven member 12 is, on the other hand, guided in axial translation in the coupling tip 20 integral with said body 2. For this purpose, the coupling tip 20 comprises a smooth cylindrical central bore 24 extending in the longitudinal axis A, open, communicating with the tapped bore 114 of the driving member 11, and in which a guide section 122 of the driven member 12 is slidably mounted, by means of an O-ring 124 and a centring bead 125. The O-ring 124 also makes it possible to provide sealing between the body 2 of the electrode 1 and the driving member 11 via the adjusting screw 120.

The driven member 12 is fixed in rotation relative to the driving member 11 and locked in rotation relative to said body 2 by means of two diametrically opposed guide pins 25 passing through a corresponding port provided in the guide section 22 and in a plane perpendicular to the longitudinal axis A. The end of each guide pin 25 cooperates with an axial slot 123 provided in the outer face of the guide section 122 of the driven member 12. These axial slots 123 extend over a determined stroke C in order to form, with the guide pins 25, stroke limiters arranged to control the axial displacement of the driven member 12 over a stroke C corresponding at least to the maximum projection length L6 of the second electrical contact elements 6. Of course, any other means for locking the driven member 12 from rotating relative to the driving member 11 and to the body 2, as well as any other stroke-limiter may be suitable.

Figure 5:
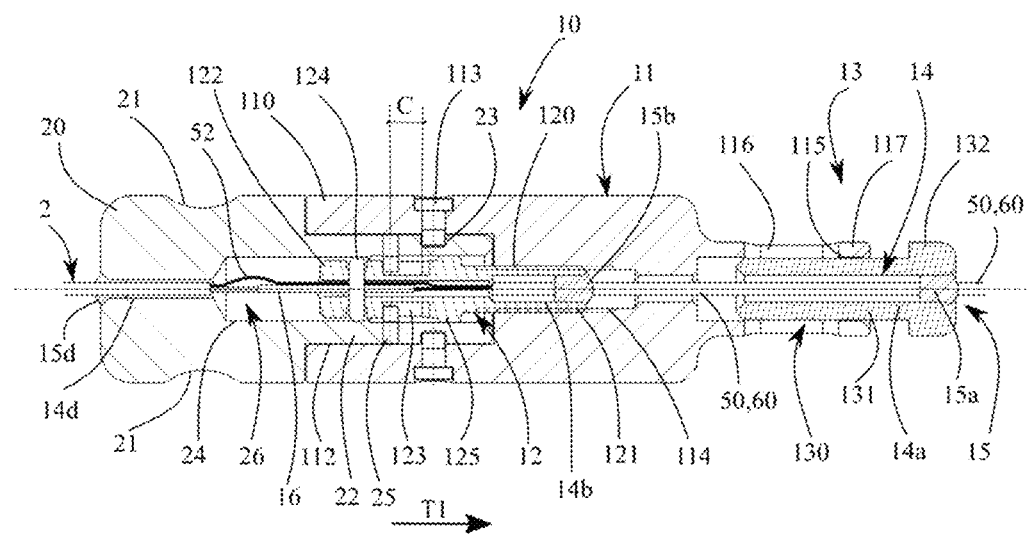
FIG. 5 is an axial cross-sectional view of the control means in FIG. 2, in a position corresponding to the passive position of the micro-contacts.
Figure 6:
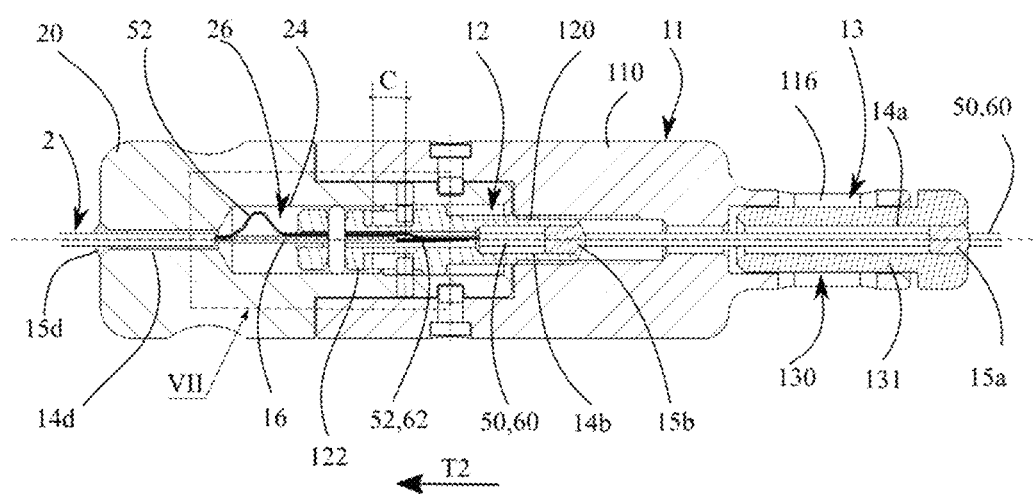
FIG. 6 is a similar view to FIG. 5, showing the control means in a position corresponding to the active position of the micro-contacts.

The central bore 24 provided in the coupling tip 20 is deeper than the length of the guide section 122 of the driven member 12, including its stroke C, for the purpose of creating a reserve 26 in which the conductor wires 52 of the first electrical contact elements 5 may accumulate freely to absorb said stroke C of the driven member 12 (see FIGS. 5 and 6).

The control means 10 also comprises a member 13 for locating the axial position of the driven member 12 and therefore the position of the second electrical contact elements 6. In the example shown in FIGS. 1 to 8, this locating member 13 takes the form of a slider 130 integral with the multi-wire sheaths 50 and 60 and mounted in axial translation in a guide bore 115 of the driving member 11, coaxial with the longitudinal axis (A, and open at the opposite end of the coupling tip 20. This slider 130 comprises a cylindrical guide section 131, terminated by a head 132, the diameter of which is greater than the diameter of the guide bore 115. The guide section 131 comprises a marking 133, engraved or printed on the outer surface, and visible through one and preferably a plurality of through-holes 116, arranged around an end section 117 of the driving member 11. This marking 133 may, for example, correspond to a millimeter graduation, representative of the outlet status of the second electrical contact elements 6 depending on the position of the adjusting screw 120. There may be four slots 116 in order to guarantee the visibility of the marking 133 regardless of the angular position of the thumbwheel 110. Of course, it may be suitable to use other forms of locating member, slide, marking and display means.

The component parts of the control means 10 are traversed by an axial housing 14 coinciding with the longitudinal axis A, coaxial with said axial housing 9 provided in the body 2, to make it possible for the conductor wires 52 and 62 to electrically connect the first electrical contact elements 5 and the second electrical contact elements 6 to a connected medical device. In order to make the free axial displacement of the conductor wires possible 52, 62 simultaneously with the driven member 12, the corresponding multi-wire sheaths 50, 60 are connected to the different moving parts 12 and 130 by means, for example, of plugs 15 arranged to close the corresponding axial bore 14 by sealing said sheaths. These plugs 15 may be formed by glue joints, inserts, or similar. Starting from the multi-contact connectors 51, 61, a first plug 15a closes the inlet of the axial housing 14a provided in the slider 130, and a second plug 15b closes the inlet of the axial housing 14b provided in the adjusting screw 120. Then, the multi-wire sheaths 50, 60 stop. The conductor wires 62 of the second electrical contact elements 6 are then secured to a guide tube 16 via a gluing area 17, itself firmly secured to the adjusting screw 120 by a third plug 15c closing the outlet of the axial housing 14b. This advantage of this guide tube 16 is that it accompanies and guides the conductor wires 62 of the second electrical contact elements 6 in their translational movement. The conductor wires 52 of the first electrical contact elements 5 are secured to the adjusting screw 120 by the third plug 15c closing the outlet of the axial housing 14b. Finally, the coupling tip 20 and the body 2 of the electrode 1 are secured by a fourth plug 15d closing the outlet of the axial bore 14d provided in the coupling tip 20. This embodiment is non-limiting, and any other equivalent means for connecting the sheaths 50, 60 to the parts 12, 13 may be used.

The control means 10 which has just been described with reference to FIGS. 1 to 8 may respond to other variant embodiments, and it is essential to provide a precise adjustment means, easily accessible to the practitioner, which generates a precise axial displacement of the second electrical contact elements 6. For example and in an embodiment (not shown), the adjusting screw 120 may be provided directly on the driving member, which in this case is coupled in rotation and in translation with the coupling tip 20 integral with the body 2 of the electrode 1. In this case, the driven member takes the form of a pusher actuated in one direction by the driving member in a first direction of rotation, and in an opposite direction by a return member when the driving member is rotated in the opposite direction of rotation.

In another variant embodiment, shown in FIGS. 9 to 13, the control means 30, 300 generates the displacement of the second electrical contact elements 6 by a single reciprocating translational movement according to the arrows T1, T2 over a stroke C at least equal to the controlled projection length L6 of the second electrical contact elements 6. To this end, the driving member 31 is a pusher 310 movable in translation relative to the body (2) along an axis parallel to or coincident with the longitudinal axis A of said body 2, and directly coupled in translation to the driven member 32 which is a slider 320 also movable in translation along the same axis parallel to or coincident with the longitudinal axis A. In this variant embodiment, the pusher 310 projects radially from a cylindrical handle 311 through a slot 312 which defines said stroke C. The construction of these control means 30 partly resumes that of the control means 10 described in detail with reference to FIGS. 1 to 8. The handle 311 is also fixed to the end piece of the body 20, perpendicular to its guide section 22, via shouldered pins 113 ending in a hole 23) The slider 320 extends from the end piece of the body 20 through the handle 311 and emerges opposite the body 2 of the electrode 1 to end in a head 132. It is guided in axial translation by guide bores 321 and 322 provided respectively in the handle 311 and in the end piece of the body 20. It is also maintained in position by friction, on the one hand, via O-rings 323 and 124 provided between the slider 320 and the handle 311, and on the other hand, between the slider 320 and the end piece of the body 20. These O-rings also ensure that this sliding connection is tightly sealed. As in the preceding example, guide pins 2) are provided between the guide section 22 of the end piece of the body 20 and the part of the slider 320 located in the end piece of the body 20 and provided with corresponding axial slots 123 extending over said stroke corresponding at least to the maximum projection length L6 of the second electrical contact elements 6. The slider 320 is engaged with the pusher 310 via a radial port 324 into which the inner end of the pusher 310 may be force-fitted, crimped, welded and/or glued, or screwed. The outer end of the slider 320 forms a member 33 for locating the axial position of the driven member 32 and therefore the position of the second electrical contact elements 6. It comprises a marking 133, engraved or printed on the outer surface, and visible through one and preferably a plurality of through-holes 116, arranged around an end section 117 of the driving member 31. It is also terminated by a head 132. The different examples of variant embodiments of the control means is non-limiting in nature.

Figure 13:
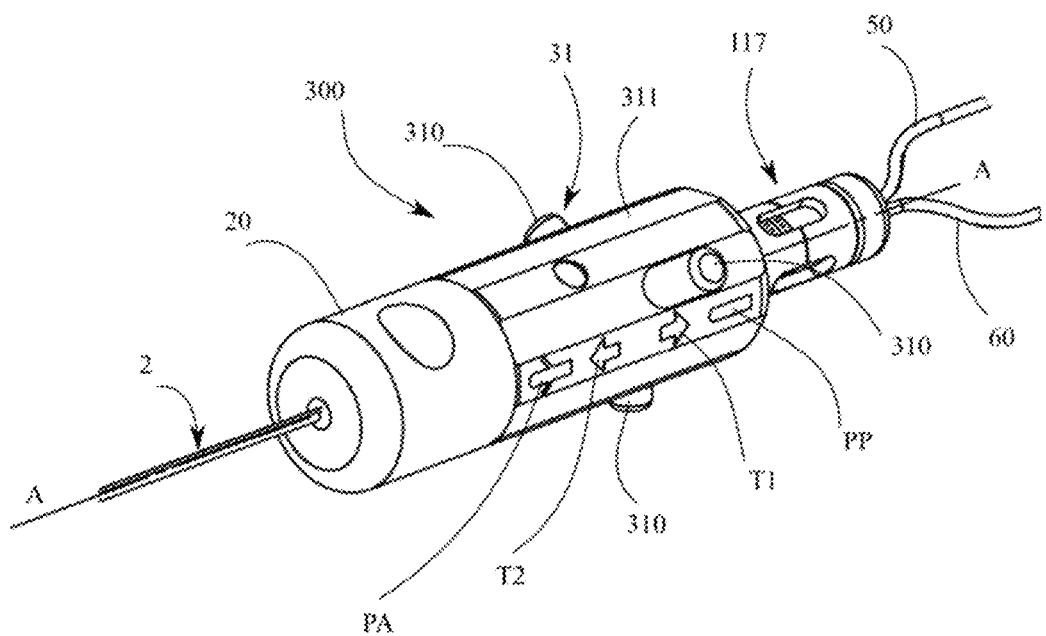
FIG. 13 is a perspective view of the control means of the micro-contacts in FIG. 9 adapted to individually control three groups of micro-contacts distributed at different levels over the active part of the electrode.
Figure 14:
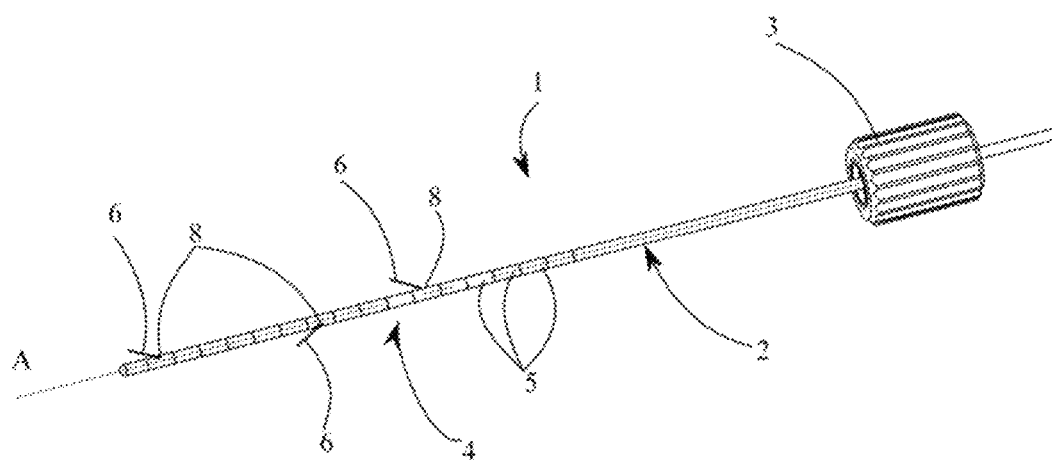
FIG. 14 is a perspective view of a hybrid intracerebral electrode according to the invention comprising three groups of micro-contacts distributed at different levels on its active part.

With reference to FIGS. 13 and 14, the active part 4 of the body 2 of the electrode 1 comprises a plurality of outlet ports 8 distributed at different levels, for example over three levels, from which second electrical contact elements 6 may exit, simultaneously or individually. For this purpose, it is possible to use the control means 10, 30 in order to simultaneously control the displacement of all second electrical contact elements 6 regardless of their level. The control means 300 may also be used to individually control the second electrical contact elements 6 by level. For this purpose, they comprise three pushers 310 distributed radially around the handle 311 and are capable of being actuated independently of one another depending on the second electrical contact elements 6 to be moved from a passive position PP to an active position PA and vice versa. In this case, each pusher 310 controls a slider 320 connected to a second electrical contact element 6. Of course, the differentiated control of these second electrical contact elements 6 may also be performed by using the control means 10 according to FIGS. 1 to 8.

The various constituent parts of the electrode 1 may be manufactured by industrial processes and be made of materials compatible depending on the mechanical, electrical and magnetic stresses, in accordance with what is currently performed in terms of existing intracranial electrodes and/or according to different processes but compatible with this application.

The protocol for implanting deep intracerebral electrodes for performing stereoelectroencephalography (SEEG) has the advantage of not requiring modifications when standard deep electrodes are replaced by hybrid deep electrodes (macro-contacts and micro-contacts) according to the invention. In fact, electrode 1 is implanted in the brain of a patient, the second electrical contact elements 6 having returned to the passive position PA. Plug 3 makes it possible for the electrode 1 implanted on a screw or similar, previously anchored in the patient's skull to be maintained in position and sealed. The multi-contact connectors 51 and 61 are connected to a medical device. The practitioner, generally a neurosurgeon, may then actuate the control means 10 to move the second electrical contact elements 6 into the active position PA, and to adjust the controlled projection length L6 of these second electrical contact elements 6 throughout the implantation of the electrode 1.

This new electrode 1 has the advantage of being able to be used as a standard deep electrode, while making much higher quality and precise exploration and processing possible. Thus, it is clear from this description that the electrode 1 according to the invention meets the objectives set and provides substantial advantages over the hybrid electrodes of the prior art.

This invention is not limited to the examples embodiment described herein, but encompasses all amendments and alternatives that are clear to a person skilled in the art. In particular, the number of first electrical contact elements 5 as well as the number of second electrical contact elements 6, the number of conductor wires grouped to form each second electrical contact element 6, the pitch between the first electrical contact elements 5, the positioning and orientation of the second electrical contact elements 6 relative to these first electrical contact elements 5, etc. are variable parameters depending on the technical specifications of the electrode 1.

The invention claimed is:

1. A hybrid intracerebral electrode comprising a body narrow and elongated along a longitudinal axis, intended to be implanted in the brain of a patient for performing at least one multi-scale electroencephalographic exploration, said electrode having a distal end and a proximal end, and an active part provided on the distal end side, said active part being provided with at least one first electrical contact element forming a fixed macro-contact, arranged on the surface of said body and used in particular for recording the activity of an area of the brain under study, and at least one second electrical contact element forming a mobile micro-contact, projecting outside said body over a controlled projection length, and used at least to record the activity of small cell groups or even of a single neuron in said area of the brain under study, said at least one first electrical contact element and said at least one second electrical contact element each being electrically connected to at least one recording device by a dedicated conductor wire, said electrode further comprising means for controlling the relative position of said at least one second electrical contact element relative to said body of the electrode, wherein said electrode comprises at a proximal end a coupling tip integral with said body and on which is mounted said control means for controlling the relative position of said at least one second electrical contact element so that they form an integral part of said electrode, and wherein said control means is arranged firstly to displace said at least one second electrical contact element between a passive position in which the at least one second electrical contact element is retracted inside said body and an active position in which the at least one second electrical contact element projects outside said body, and secondly to adjust the controlled projection length of said at least one second electrical contact element relative to said body of the electrode, wherein said control means comprises at least one driving member movable in rotation relative to said coupling tip around a rotation axis coincident with the longitudinal axis of said body, and a driven member coupled to said driving member so as to be displaced in reciprocating axial translation in the direction of rotation of said driving member, and wherein said driven member is integral with said at least one second electrical contact element so that the at least one second electrical contact element is movable in translation in the longitudinal axis of said body over a stroke at least equal to the controlled projection length of the at least one second electrical contact element, and wherein said driving member takes the form of a thumbwheel which may be actuated manually, coupled in rotation with said coupling tip by a thread, and movable in translation relative to said coupling tip.

2. The electrode according to claim 1, wherein said driven member takes the form of a pusher actuated in one direction and in an opposite direction according to the direction of rotation of said driving member.

3. The electrode according to claim 1, wherein said control means comprises stroke limiters arranged in order to control an axial displacement of the driven member over a stroke at least equal to the controlled projection length of said at least one second electrical contact element.

4. The electrode according to claim 3, wherein said stroke limiters comprise at least one axial slot extending over a length corresponding to said stroke and cooperating with at least one guide pin, said axial slot being provided in one of the parts of said driven member or of said coupling tip, and said guide pin being provided in the other part of said coupling tip or of said driven member.

5. The electrode according to claim 1, wherein said coupling tip comprises a central bore in which the driven member is guided in axial translation and wherein said central bore defines a reserve in which the conductor wire dedicated to said at least one first electrical contact element may accumulate in order to absorb the travel of said driven member.

6. The electrode according to claim 1, wherein said control means comprises means for locating an outlet position of said at least one second electrical contact element.

7. The electrode according to claim 6, wherein said locating means comprises a slider integral with said at least one second electrical contact element and arranged to slide axially in a guide bore of said coupling tip or of a driving member, said slider comprise a marking and said guide bore comprise at least one through-hole for displaying said marking.

8. The electrode according to claim 1, wherein said body comprises at least one outlet port provided in the active part of the electrode, through which said at least one second electrical contact element projects outside said body in the active position.

9. The electrode according to claim 8, wherein the active part of the electrode comprises a plurality of first electrical contact elements distributed along the body of the electrode and separated from one another by intermediate insulating elements, and wherein the said at least one second electrical contact element projects through the said at least one outlet port provided in the said active part in one of the said intermediate insulating elements and/or in one of the said first electrical contact elements.

10. The electrode according to claim 8 wherein said at least one outlet port is provided on the periphery of said body and wherein said at least one second electrical contact element projects radially outside said body relative to the longitudinal axis.

11. The electrode according to claim 10, wherein the active part of the electrode comprises at least two second electrical contact elements distributed radially around said body.

12. The electrode according to claim 8, wherein the said active part comprises a plurality of second electrical contact elements grouped at least by two to exit through a same outlet port.

13. The electrode according to claim 8, wherein said active part comprises a plurality of outlet ports distributed over at least two levels along the body of the electrode and wherein said control means is arranged to individually or simultaneously control the second electrical contact elements per level.

14. A hybrid intracerebral electrode comprising a body narrow and elongated along a longitudinal axis, intended to be implanted in the brain of a patient for performing at least one multi-scale electroencephalographic exploration, said electrode having a distal end and a proximal end, and an active part provided on the distal end side, said active part being provided with at least one first electrical contact element forming a fixed macro-contact, arranged on the surface of said body and used in particular for recording the activity of an area of the brain under study, and at least one second electrical contact element forming a mobile microcontact, projecting outside said body over a controlled projection length, and used at least to record the activity of small cell groups or even of a single neuron in said area of the brain under study, said at least one first electrical contact element and said at least one second electrical contact element each being electrically connected to at least one recording device by a dedicated conductor wire, said electrode further comprising means for controlling the relative position of said at least one second electrical contact element relative to said body of the electrode, wherein said electrode comprises at a proximal end a coupling tip integral with said body and on which is mounted said control means for controlling the relative position of said at least one second electrical contact element so that they form an integral part of said electrode, and wherein said control means is arranged firstly to displace said at least one second electrical contact element between a passive position in which the at least one second electrical contact element is retracted inside said body and an active position in which the at least one second electrical contact element projects outside said body, and secondly to adjust the controlled projection length of said at least one second electrical contact element relative to said body of the electrode, wherein said control means comprises at least one driving member movable in reciprocating axial translation and/or in rotation relative to said coupling tip along an axis parallel to or coincident with the longitudinal axis of said body, and a driven member coupled to said driving member so as to be displaced in reciprocating axial translation in the direction of displacement of said driving member, and wherein said driven member is integral with said at least one second electrical contact element so that the at least one second electrical contact element is movable in translation along the longitudinal axis of said body over a stroke at least equal to the controlled projection length of the at least one second electrical contact element, wherein said coupling tip comprises a central bore in which a driven member is guided in axial translation and wherein said central bore defines a reserve in which the conductor wire dedicated to said at least one first electrical contact element may accumulate in order to absorb the travel of said driven member.

15. The electrode according to claim 14, wherein the said driving member takes the form of a thumbwheel which may be actuated manually, coupled in rotation with said coupling tip by a guide surface, and fixed in axial translation relative to said coupling tip.

16. The electrode according to claim 15, wherein said driven member takes the form of an adjusting screw guided axially in said coupling tip, coupled in translation with said driving member by a thread, and fixed in rotation relative to said driving member.

17. A hybrid intracerebral electrode comprising a body narrow and elongated along a longitudinal axis, intended to be implanted in the brain of a patient for performing at least one multi-scale electroencephalographic exploration, said electrode having a distal end and a proximal end, and an active part provided on the distal end side, said active part being provided with at least one first electrical contact element forming a fixed macro-contact, arranged on the surface of said body and used in particular for recording the activity of an area of the brain under study, and at least one second electrical contact element forming a mobile micro-contact, projecting outside said body over a controlled projection length, and used at least to record the activity of small cell groups or even of a single neuron in said area of the brain under study, said at least one first electrical contact element and said at least one second electrical contact element each being electrically connected to at least one recording device by a dedicated conductor wire, said electrode further comprising means for controlling the relative position of said at least one second electrical contact element relative to said body of the electrode, wherein said electrode comprises at a proximal end a coupling tip integral with said body and on which is mounted said control means for controlling the relative position of said at least one second electrical contact element so that they form an integral part of said electrode, and wherein said control means is arranged firstly to displace said at least one second electrical contact element between a passive position in which the at least one second electrical contact element is retracted inside said body and an active position in which the at least one second electrical contact element projects outside said body, and secondly to adjust the controlled projection length of said at least one second electrical contact element relative to said body of the electrode, wherein said control means comprises at least one driving member movable in reciprocating axial translation and/or in rotation relative to said coupling tip along an axis parallel to or coincident with the longitudinal axis of said body, and a driven member coupled to said driving member so as to be displaced in reciprocating axial translation in the direction of displacement of said driving member, and wherein said driven member is integral with said at least one second electrical contact element so that the at least one second electrical contact element is movable in translation along the longitudinal axis of said body over a stroke at least equal to the controlled projection length of the at least one second electrical contact element, wherein said control means comprises means for locating an outlet position of said at least one second electrical contact element, and wherein said locating means comprises a slider integral with said at least one second electrical contact element and arranged to slide axially in a guide bore of said coupling tip or of a driving member, said slider comprise a marking and said guide bore comprise at least one through-hole for displaying said marking.

\* \* \* \* \*